United States Patent [19]

Harhen et al.

[11] Patent Number: 5,326,272
[45] Date of Patent: Jul. 5, 1994

[54] LOW PROFILE ELECTRODE CONNECTOR

[75] Inventors: Robert P. Harhen; William J. Marlow, both of Andover; Dawn E. Sissom, Lexington, all of Mass.

[73] Assignee: Medtronic, Inc., Minneapolis, Minn.

[21] Appl. No.: 636,830

[22] Filed: Jan. 2, 1991
(Under 37 CFR 1.47)

Related U.S. Application Data

[63] Continuation-in-part of Ser. No. 472,504, Jan. 30, 1990, abandoned.

[51] Int. Cl.⁵ .................................................. A61B 5/04
[52] U.S. Cl. ...................................... 439/86; 128/641; 439/859; 439/909
[58] Field of Search .................... 439/37, 86, 374, 592, 439/593, 859, 909; 128/639, 640, 641, 642, 643, 802; 24/669, 702

[56] References Cited

U.S. PATENT DOCUMENTS

| | | | |
|---|---|---|---|
| 1,261,588 | 4/1918 | Mittelstadt | 24/661 |
| 1,428,358 | 9/1922 | Burbery | 24/702 |
| 3,566,860 | 3/1971 | Moe | |
| 3,606,881 | 9/1971 | Woodson | |
| 3,828,766 | 8/1974 | Krasnow | |
| 3,964,469 | 6/1976 | Manley | |
| 3,995,644 | 12/1976 | Parsons | 128/784 |
| 4,026,278 | 5/1977 | Ricketts et al. | |
| 4,166,453 | 9/1979 | McClelland | 128/639 |
| 4,237,886 | 12/1980 | Sakurada et al. | 128/303.13 |
| 4,253,721 | 3/1981 | Kaufman | 439/909 |
| 4,268,101 | 5/1981 | Stone | 439/86 |
| 4,273,135 | 6/1981 | Larimore et al. | 128/640 |
| 4,282,878 | 8/1981 | Novello | 128/641 |
| 4,490,005 | 12/1984 | Hovey | 128/641 |
| 4,671,591 | 7/1985 | Archer | 128/641 |
| 4,674,511 | 5/1984 | Cartmell | 128/640 |
| 4,676,561 | 6/1987 | Barrett, II | 439/37 |
| 4,685,467 | 8/1987 | Cartmell et al. | 128/640 |
| 4,757,817 | 3/1987 | Healy | 128/641 |

FOREIGN PATENT DOCUMENTS 2453512  3/1980  France .

Primary Examiner—Neil Abrams
Attorney, Agent, or Firm—Daniel W. Latham; Harold R. Patton

[57] ABSTRACT

A low profile connector, as for an electrode, is disclosed. The connector of the invention includes an electrically conductive connector body and electrical connector means to separate electronics. The connector body has a channel or groove which communicates with one side of the connector body and its bottom. The channel leads to a "stop" position located substantially the central portion of said body. Viewed from the bottom of the connector body, the channel is interiorly concave so as to cooperatively, preferably rotatively and restrictively receive and hold an upstanding portion of an electrode, such as an electrode eyelet. In a preferred aspect, the present invention is an electrical assembly which includes the connector body and a biomedical electrode, such as a TENS electrode.

16 Claims, 2 Drawing Sheets

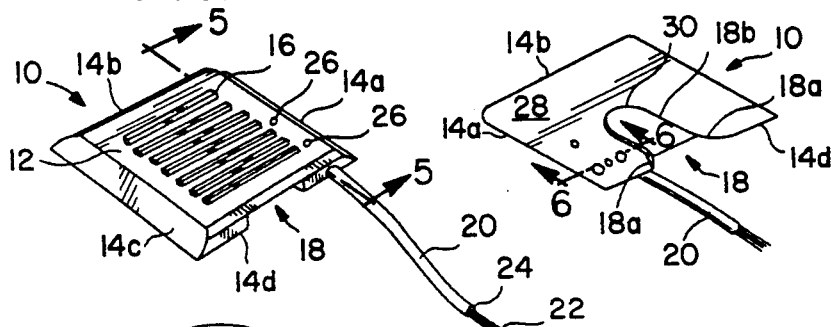
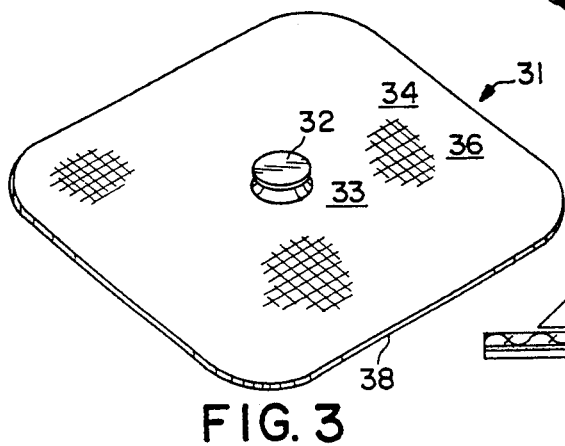
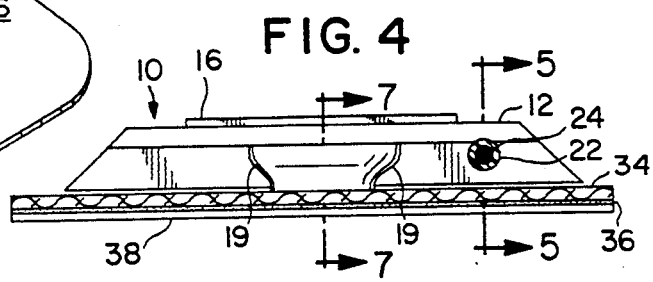
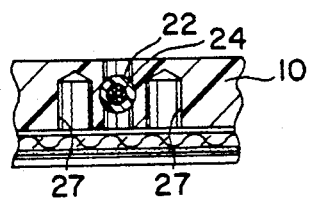
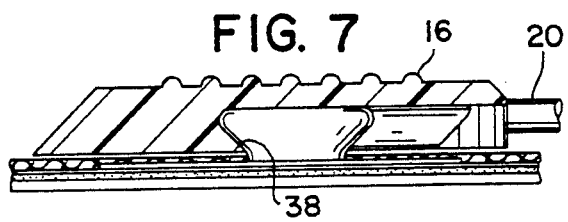

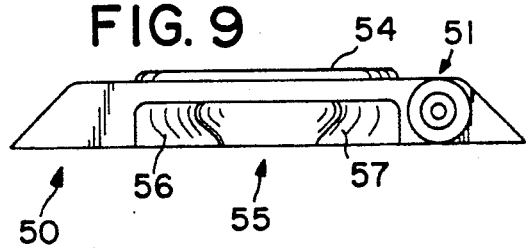
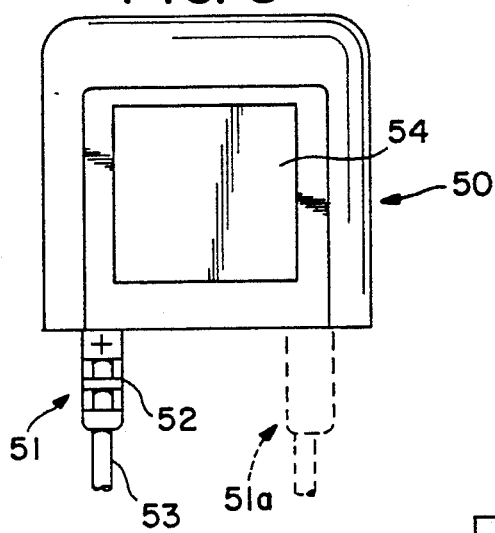
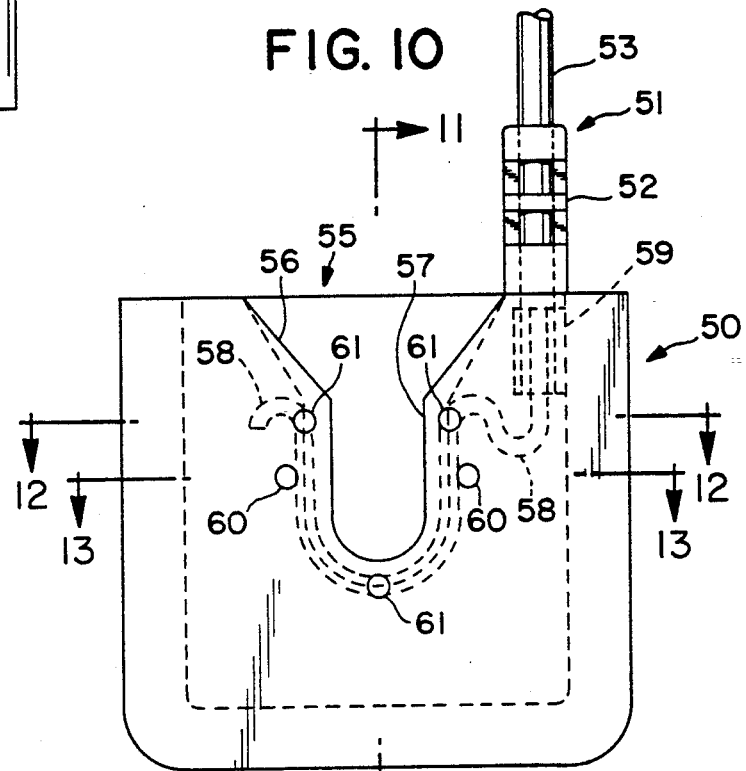
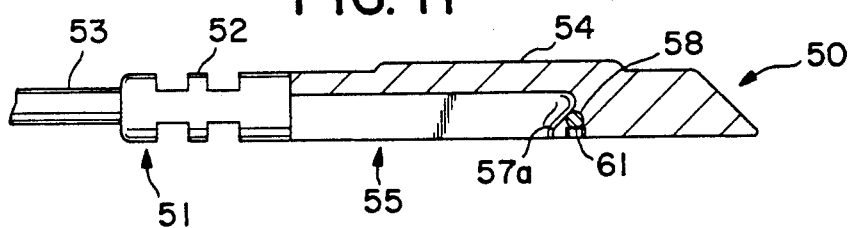
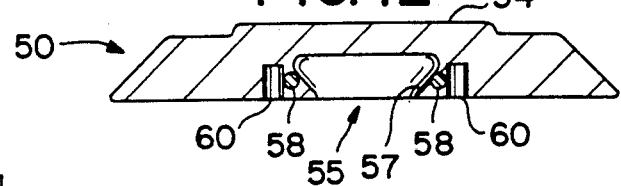
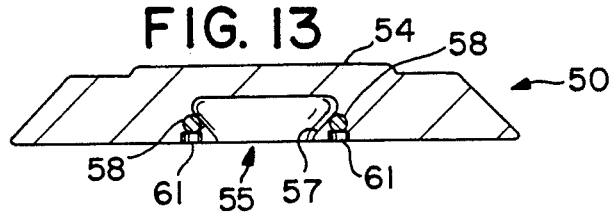

LOW PROFILE ELECTRODE CONNECTOR

This is a continuation-in-part of copending application Ser. No. 07/472,504 filed on Jan. 30, 1990, now abandoned.

BACKGROUND OF THE INVENTION

This invention relates to low profile connectors especially useful in the biomedical field. More specifically, this invention relates to preferably rotatable, restriction fit electrode connectors or adapters that are particularly useful to connect transcutaneous electronic nerve stimulator (TENS) electrodes to suitable electrical signal generating means. (Electromyographic, and sensing, monitoring or stimulating electrodes could also be connected or coupled in a practice of this invention.) Even more particularly, this invention relates to restriction fit electrode connector assemblies or adapters in which a connector body slides over an upstanding member, e.g., a bulbous post, of an electrode, "snapping" into place so as to permit secure, rotatable electrical coupling between the connector and the electrode.

There are many types of connectors used in the medical industry to connect various skin interface means, e.g., TENS electrodes, monitoring and diagnostic ECG electrodes, to separate electrical means. Such separate electrical means could include electrical pulse generators, or signal processors. In many instances, these connectors permit the user to employ relatively inexpensive disposable electrodes with relatively more expensive connector means which can then be reused. None of these connectors have the advantages of the present invention, viz., a low profile, a secure coupling or connection, preferably rotatable restriction fit and ease of detachment from the electrode once the electrical measurement has been completed.

BRIEF SUMMARY OF THE INVENTION

Briefly, in one aspect the present invention is a connector for slidable and preferably rotatable conductive engagement with an upstanding connecting member of an electrode, the connector comprising:

an at least partially conductive connector body having a multiplicity of sides, a top and a bottom, the connector body having therein a channel. The channel communicates with one side and the bottom of the body so as to slidably and restrictively receive the member while preferably permitting rotation between the body and the electrode. The channel has a widened portion opening to the one side and tapering to a narrower portion, the narrower portion of the channel having substantially non-parallel sides (including partially hemispherical) and a terminus at approximately the center of the connector body. The channel may also be characterized as interiorly concave so as to cooperate with and electrically and physically couple with the member; and electrical connector means for connecting said connector body to separate electrical input or output means.

In a preferred aspect, the connector body of the present invention has a grip means on the top thereof so as to provide ease of connector-electrode coupling and decoupling. In yet another preferred practice of the present invention, the connector body is substantially square, having four sides.

In yet another aspect, this invention comprises a connector assembly comprising the above-described connector and a cooperative skin interface means having, as a minimum, an upstanding member, stud or post. The cooperating, upstanding member provides electrical coupling to the electrode structure, itself. In the most preferred practice of this invention, the skin interface means is a TENS electrode.

BRIEF DESCRIPTION OF THE DRAWINGS

FIG. 1 is a perspective view of the top of the electrical connector or adaptor of present invention;

FIG. 2 is a perspective view of the bottom of the connector of the present invention;

FIG. 3 is a perspective view of a typical TENS electrode;

FIG. 4 is a fragmentary front elevational view of the present invention with an electrode assembly coupled thereto;

FIG. 5 is a fragmentary section taken along line 5—5 in FIGS. 1 and 4, respectively;

FIG. 6 is a fragmentary section taken along line 6—6 in FIG. 2 and FIG. 5;

FIG. 7 is a fragmentary section taken along line 7—7 in FIG. 4;

FIG. 8 is a top plan view of an embodiment of the invention showing alternate lead position in dashed line;

FIG. 9 is an elevational view of the embodiment of FIG. 8;

FIG. 10 is a bottom plan view of the embodiment of FIG. 8;

FIG. 11 is a sectional side view taken along line 11—11 in FIG. 10;

FIG. 12 is a sectional rear elevational view taken along line 12—12 of FIG. 10; and FIG. 13 is a sectional rear elevational view taken along line 13—13 of FIG. 10.

DETAILED DESCRIPTION OF THE INVENTION

Referring now to FIGS. 1 and 2, there is shown perspective views of a conductive connector body 10 of the present invention. FIG. 1 shows a top view of a connector body 10 of the invention which, in this depiction, comprises a top 12 and four sides 14a–14d. As shown, primarily for aesthetic reasons, sides 14a–14d may be chamfered or beveled. Connector body 10 may be of other geometric shapes, e.g., triangular, circular, semicircular or polygonal, within the contemplation of the present invention. FIG. 1 also shows an optional grip means which, in this embodiment is a series of substantially parallel, raised ridges 16. Other such grip means (possibly including texturing, indentations or bumps in or on top 12 of connector body 10) would be readily suggested to one of skill in this art. The grip means is intended to make utilization of the present connector with a finger or thumb substantially easier. In side 14d of connector body 10 there is shown channel or groove 18. Channel 18 is more completely described hereinbelow. Lastly, connector body 10 further includes electrical connector means which in this embodiment is electrical lead 20. Electrical lead 20 comprises input wire 22 having electrical insulation 24 therearound. Electrical lead 20 may be permanent (as shown) or temporary comprising cooperating couplers or connectors within connector body 10 and on the distal end of electrical lead 20.

Connector body. 10, as shown, has one or more holes 26. Pins in holes 26 secure wire 22 in place during molding so that, in profile, wire 22 would have an "S" configuration (top to bottom) inside connector having an "S" configuration (top to bottom) inside connector body 10 This "S" configuration, see FIG. 10, provides better mechanical coupling between connector body 10 and electrical lead means 20. Connector body 10 is itself at least partially conductive (connector body 10 need not be entirely conductive), thus providing efficient electrical coupling or connection between a biomedical electrode and separate electrical devices. (It is to be understood that the other end of electrical lead 20 normally terminates in some other sort of connector (not shown) which would, in turn, plug into the separate electrical device.)

FIG. 2 shows a bottom view of connector body 10. Connector body underside or bottom 28 has channel or groove 18 therein. Although channel 18 does not extend all the way through connector body 10 (nor through top 12), it is conceivable that it could do so. Channel 18 is in communication with one side (14d) of connector body 10 and leads approximately to the center of the bottom 28 thereof. Channel 18 has a wider portion 18a adjacent the region where it intersects side 14d and narrows 18b to a semi-circular terminus or stop 30. Stop 30 would abut an upwardly projecting portion of a biomedical electrode, e.g., a bulbous post, and provide a secure restriction fit therefor. The composition of the connector body 10 is chosen so as to provide sufficient resilience or compressibility in the sides 18a–18b of channel 18 and stop 30 to cause, e.g., an electrode post, to "snap" into place adjacent stop 30, thereby providing a secure restriction fit.

FIG. 3 shows a typical TENS electrode 31 that could be employed with the present connector. Electrode 31 comprises upstanding connecting member which, in this embodiment, is a circular, bulbous post 32. Electrode 31 further includes a backing member 34 which could be constructed of a flexible, breathable, material such as spunlace. Overlying the base portion of post 32 would be a conductive adhesive gel 36. In this embodiment, the adhesive gel is a poly AMPS gel commercially available from the Promeon Division of Medtronic, Inc. under the designation RG-62D. Other commercially available polymeric or natural conductive gels would be suitable for this application. Completing this TENS electrode construction is a release liner 38. Release liner 38 could, for example, be release coated "Mylar" polyester film. Post 32 is likely to have a larger, circular base section 33 (shown in shadow on FIG. 2) which provides current distribution capability to the electrode. Post 32 is silver plated plastic, thereby providing electrical connection to conductive gel 36. Post 32 may be made of any conductive plastic or other conductive material. The particular details of the construction of an electrode for use in the present invention are not critical with the exception that any such electrode must have an upstanding male connector member. U.S. Pat. No. 4,273,135, the details of which are incorporated by reference herein, is one of many possible electrode constructions that could be used in the practice of this invention. In operation then, the release liner 38 would be removed from the electrode and the electrode placed on a patient's skin. The electrode then would be electrically coupled or connected to an electronic nerve stimulator by means of connector 10.

FIG. 4 shows a view of the present invention looking approximately straight into channel 18. Electrode 31 is shown after it has been "snapped" into connector 10. As is shown in FIG. 4, the sides or walls 19 of channel 18 are substantially non-parallel. Channel 18 is interiorly concave (as viewed essentially normal from bottom 28), being, in the embodiment, approximately truncated triangular in cross section. The interior shape of channel 18 is selected so as to prevent detachment or lifting off of connector body 10 from the cooperating upstanding member of the electrode which is employed. Various other concave configurations could be used for channel 18 provided connector body 10 is adequately secured to the upstanding member. For example, a keyhole shaped interior (i.e., cross-like in section) could be utilized. The configuration for channel 18 adjacent stop 30 permits it to receive and restrictively hold the upstanding member of an electrode. Electrode 31, by virtue of the present invention and the fact that upstanding member 32 is circular, can be freely rotated with respect to connector 10. This is particularly advantageous in application because it permits the patient to be mobile without interrupting the intended therapy.

FIG. 5 shows a fragmentary section taken along line 5—5 in FIGS. 1 and 4. FIG. 5 shows wire 22 insulatively enshrouded by insulator 24. Also shown is metal sheath 40 which, in construction of the invention, is wrapped around wire 22 to enhance electrically coupling to connector body 10. Metal sheath 40 is a preferred means to integrally connect wire 22 to connector body 10 because it provides a more secure anchor therewith.

As is most clearly shown in FIG. 6, there are holes 27 upwardly projecting from the bottom 28 of connector body 10. These holes 27 allow insertion of pins to restrict left-to-right movement of lead wire 20 within connector body 10 while connector body 10 is being molded. After molding is completed, the pins are withdrawn, leaving holes 27 and lead wire molded in connector body 10.

FIG. 7 is a fragmentary section taken along line 7—7 of FIG. 4. The circular stop 30 which is centrally disposed in connector body 10 is clearly shown. Grip means 16 and its relationship to electrical connector means 20 also are shown.

Referring now to the embodiment depicted in FIGS. 8-13 in which a metal wire acts as an electrically conductive element, FIG. 8 is a top plan view of this embodiment of the invention. Depicted in FIG. 8 is a connector 50 having an electrical lead 51 which provides an electrical connection with an electrical input or output (not shown). The electrical lead 51 comprises a strain relief portion 52 and a wire portion 53. Alternatively, the electrical lead 51 may be positioned elsewhere on the connector 50; for example, in the position of the electrical lead 51a. Also shown is a raised central portion 54 to which indicia (not shown) may be optionally applied, such as, for example, the trademark of the manufacturer.

FIG. 9 is an elevational view of the embodiment of FIG. 8. Depicted in FIG. 9 is the connector 50 the electrical lead 51, and the raised central portion 54. Also depicted is a channel 55 having a wider portion 56 and a narrower portion 57.

FIG. 10 is a bottom plan view of the embodiment of FIG. 8. FIG. 10 depicts the connector 50 and the electrical lead 51 with strain relief portion 52 and wire portion 53. Also depicted is the channel 55, the wider channel portion 56, the narrower channel portion 57 and a terminis or stop portion 57a. Also depicted is an electrically conductive metal wire 58 and a connector block 59 through which the wire 58 is connected to the electrical lead 51. The wire 58 extends from the connector block 59 to the narrower portion 57 of the channel 55 and along the narrower portion 57 and the stop portion 57a such that electrical contact may be achieved between the wire 58 and the upstanding connecting member 32 shown in FIG. 3 when the upstanding connecting member 32 is received in the narrower portion 57 of the channel 55. Also depicted in FIG. 10 are first recesses 60 and second recesses 61. The recesses 60, 61 are present due to the use of pins in the mold (not shown) to retain the wire 58 in a correct portion during the molding process for the connector 50 and do not serve any function in the finished connector 50.

FIG. 11 is a sectional side view taken along line 11—11 of FIG. 10. Depicted in FIG. 11 is the connector 50 and the electrical lead 51 with its strain relief portion 52 and wire portion 53. Also depicted is the central raised portion 54, the metal wire 58, a second recess 61, and the channel 55 with its stop portion 57a. It should be noted that a pin in the mold (not shown) which formed the second recess 61 during the molding process that formed the connector 50 has provided support for the wire 58 such that the wire 58 is located at the surface of the stop portion 57a of the channel 55 and such that the wire 58 may be in electrical contact with the upstanding connecting member 32 when it is fully received in the channel 55 against the stop portion 57a.

FIG. 12 is a sectional rear elevational view taken along line 12—12 of FIG. 10. FIG. 12 depicts the connector 50, the raised central portion 54, the channel 55 at the narrower portion 57, the wire 58 and first recesses 60. It should be noted that pins in the mold (not shown) which formed the first recesses 60 during the molding process that formed the connector 50 provided lateral support for the wire 58 during the molding process such that the wire 58 is located at the surface of the narrower portion 57 of the channel 55 and that such electrical contact may be achieved between the wire 58 and the upstanding connecting member 32 when in FIG. 3 when the upstanding connecting member 32 is received in the narrower portion 57 of the channel 55.

FIG. 13 is a sectional rear elevational view taken along line 13—13 of FIG. 10. FIG. 13 depicts the connector 50, the raised central portion 54, the channel 55 at the narrower portion 57, the wire 58 and second recesses 61. Again, the pins in the mold (not shown) which formed the second recesses 61 provided support for the wire 58 during the molding of the connector 50.

The connector or adaptor of this invention may comprise conductive thermoplastic. A preferred material for use in molding the part is carbon loaded polypropylene. This material, which is easy to work with and which is readily commercially available, is particularly electrically suited to the TENS application. Many other conductive thermoplastic or thermosetting polymeric (or other) materials may be employed to produce the present connector within the teaching of this invention. Unmoldable conductive materials, e.g., metal, may also be employed.

It is noted from the several views, that electrical connector 20 projects into connector body 10, and is offset and on the same side (14d) as channel 18. As discussed above, connector 20 is molded into connector body 10. This is done by conventional insert molding techniques. If a non-moldable conductive material is used, a suitable orifice connector would have to be prepared. While the separation between channel 18 and the connector 20 is not particularly critical, it should be on the order of about 0.15 cm.

In a preferred practice of this invention, channel 18 and electrical connector 20 are on the same side of connector body 10 or are at least adjacent each other depending upon the shape of connector 10. It is conceivable that channel 18 and electrical connector 20 could be spatially separated.

The connector or adaptor of the present invention is low profile. As the name suggests, this simply means that this connector permits efficient electrical connection with an electrode without upwardly projecting a substantial distance from the back of such electrode. This is particularly advantageous because in this manner interference with clothing and other patient activities is minimized.

The above description of the invention is intended to illustrate and not to restrict its scope. Many other variations will occur to one of skill in this art in view of this disclosure. All such variations are to be construed as within the following claims.

We claim:

1. A connector for slidable and electrically conductive engagement with an upstanding connecting member of an electrode, the connector comprising:

a connector body having a multiplicity of sides, a top and bottom, the connector body having therein a channel, the channel communicating with one side and the bottom of said body so as to slidably and restrictively receive said member while permitting rotation said body and said electrode, the channel having a widened portion opening to the one side and tapering to a narrower portion, said narrower portion of said channel having a terminus at approximately the center of said connector body, and being interiorly concave so as to cooperate with said member;

electrical conductor means for connecting said connector body to separate electrical input or output means, said electrical conductor means attached to and extending into said connector body at a point adjacent the channel opening; and means for electrically connecting said electrical conductor means to said channel.

2. A connector according to claim 1 wherein the means for electrically connecting said electrical conductor means to said channel comprises an elcetrically conductive polymeric material.

3. A connector according to claim 2 wherein the polymeric material is carbon loaded polypropylene.

4. A connector according to claim 1 wherein the means for electrically connecting said electrical conductor means to said channel comprises an electrically conductive metal.

5. A connector according to claim 4 wherein the metal comprises a wire extending around a substantially circular terminus of the channel such that the upstanding connector member contacts the wire.

6. A connector according to claim 1 wherein the connector body has grip means on the top thereof.

7. A connector according to claim 1 wherein the connector body is substantially square, having four sides.

8. A connector according to claim 1 wherein the narrow portion of said channel in said connector body is, in cross section, a truncated triangle with the longer edge thereof being interior said connector body.

9. A connector assembly for a biomedical electrode comprising a connector body and a biomedical electrode, the connector comprising:

a connector body having a multiplicity of sides, a top and a bottom, the connector body having therein a channel, the channel communicating with one side and the bottom of said body so as to slidably and restrictively receive said member while permitting rotation between said body and said electrode, the channel having a widened portion opening to the one side and tapering to a narrower portion, said narrower portion of said channel having a substantially circular terminus at approximately the center of said connector body, said channel being interiorly concave so as to cooperate with said member;

electrical conductor means for connecting said connector body to external electrical input or output means, said electrical conductor means attached to and extending into said connector body at a point adjacent the channel opening and means for electrically connecting said electrical conductor means to said channel; and the biomedical electrode comprising:

a backing member, the backing member having on one side thereof;

conductive material to make electrical contact with skin; and adhesive material for adhering said backing member to skin;

the electrode further comprising:

an upstanding connecting member extending through said banking member which is electrically coupled to said conductive material.

10. A connector assembly according to claim 9 wherein the means for electrically connecting said electrical conductor means to said channel comprises an electrically conductive polymeric material.

11. A connector assembly according to claim 10 wherein the polymeric material is carbon loaded polypropylene.

12. A connector assembly according to claim 9 wherein the means for electrically connecting said electrical conductor means to said channel comprises an electrically conductive metal.

13. A connector assembly according to claim 12 wherein the metal comprises a wire extending around the substantially circular terminus of the channel such that the upstanding connector member contacts the wire.

14. A connector assembly according to claim 9 wherein the biomedical electrode is a TENS electrode.

15. A connector assembly according to claim 9 wherein the upstanding connecting member is a post.

16. A connector assembly according to claim 9 wherein the upstanding connecting member is a bulbous post.

* * * * *